(12) United States Patent
Rubin

(10) Patent No.: US 10,123,975 B1
(45) Date of Patent: *Nov. 13, 2018

(54) **SINGLE SOLID ORAL DOSAGE FORMS FOR TREATING *HELICOBACTER PYLORI* INFECTION AND DUODENAL ULCER DISEASE**

(71) Applicant: Darren Rubin, Largo, FL (US)

(72) Inventor: Darren Rubin, Largo, FL (US)

( * ) Notice: Subject to any disclaimer, the term of this patent is extended or adjusted under 35 U.S.C. 154(b) by 51 days.

This patent is subject to a terminal disclaimer.

(21) Appl. No.: 15/616,494

(22) Filed: Jun. 7, 2017

Related U.S. Application Data

(63) Continuation-in-part of application No. 14/463,776, filed on Aug. 20, 2014, now Pat. No. 9,700,514.

(51) Int. Cl.
| | |
|---|---|
| *A61K 9/48* | (2006.01) |
| *A61K 31/43* | (2006.01) |
| *A61K 31/426* | (2006.01) |
| *A61K 31/4164* | (2006.01) |
| *A61K 31/341* | (2006.01) |
| *A61K 9/00* | (2006.01) |
| *A61K 31/431* | (2006.01) |
| *A61K 31/496* | (2006.01) |
| *A61K 31/4439* | (2006.01) |
| *A61K 31/7048* | (2006.01) |
| *A61K 31/424* | (2006.01) |

(52) U.S. Cl.
CPC .......... *A61K 9/4891* (2013.01); *A61K 9/0053* (2013.01); *A61K 31/341* (2013.01); *A61K 31/4164* (2013.01); *A61K 31/424* (2013.01); *A61K 31/426* (2013.01); *A61K 31/43* (2013.01); *A61K 31/431* (2013.01); *A61K 31/4439* (2013.01); *A61K 31/496* (2013.01); *A61K 31/7048* (2013.01)

(58) Field of Classification Search
None
See application file for complete search history.

*Primary Examiner* — Thor B Nielsen

(57) ABSTRACT

The present invention provides improved pharmaceutical formulations for the treatment of *Helicobacter pylori* infection and duodenal ulcer disease, and includes methods of preparation and methods of medicinal use of at least one proton pump inhibitor and at least two different antibiotics within the same solid oral dosage form, whereby at least one antibiotic is coated or encapsulated independently from at least one other antibiotic within this solid oral dosage form.

26 Claims, No Drawings

SINGLE SOLID ORAL DOSAGE FORMS FOR TREATING *HELICOBACTER PYLORI* INFECTION AND DUODENAL ULCER DISEASE

RELATED APPLICATION

The present application is a continuation-in-part of pending U.S. patent application Ser. No. 14/463,776 filed Aug. 20, 2014, the subject matter of which application is incorporated herein by reference.

FIELD OF THE INVENTION

The present invention provides improved pharmaceutical formulations for the treatment of *Helicobacter pylori* infection and duodenal ulcer disease, and includes methods of preparation and methods of medicinal use of at least one proton pump inhibitor and at least two different antibiotics within the same solid oral dosage form, whereby at least one antibiotic is coated or encapsulated independently from at least one other antibiotic within this solid oral dosage form.

BACKGROUND OF THE INVENTION

*Helicobacter pylori* is a spiral-shaped, Gram-negative, microaerophilic bacterium found in the stomach and upper gastrointestinal tract of perhaps more than half of the world's population. Many with this infection are asymptomatic, yet *Helicobacter pylori* can cause chronic gastritis in children and adults, and is associated with an increased risk of developing gastric cancer and mucosal-associated-lymphoid-type (MALT) lymphoma. Unbeknownst to the medical community for many years, this bacterium was responsible for most cases of duodenal and peptic ulcers. These ulcers are associated with pain, indigestion, nausea, and loss of appetite. Bleeding from these ulcers could cause fatigue from anemia, and blood may show up in the vomit and stool. Before this bacterium was discovered, gastric and intestinal ulcers were thought to be caused mainly by spicy foods, stress, and excessive stomach acid secretion. Patients were given long-term medications, such as histamine H2-receptor antagonists (H2-blockers) and proton pump inhibitors, without a chance for permanent cure. Although these medications relieve ulcer-related symptoms, heal gastric mucosal inflammation, and may heal the ulcer, H2-blockers and proton pump inhibitors do not treat the infection and ulcers often reoccur, especially when acid suppression is removed. Only antibiotics have the potential to cure a *Helicobacter pylori* infection and prevent ulcer reoccurrence. It is believed that once this bacterium is eliminated, so is the chronic inflammation in the walls of the stomach and intestine that make these tissues more vulnerable to damage caused by digestive juices. Importantly, it was found that higher levels of acid suppression achieved with a proton pump inhibitor could potentiate the activity of antibiotics used to eradicate *Helicobacter pylori* infection. Modern regimens of eradicating *Helicobacter pylori* infection therefore include a proton pump inhibitor and antibiotics.

Proton pump inhibitors suppress stomach acid secretion by inhibiting or irreversibly blocking the hydrogen/potassium adenosine triphosphatase enzyme system of the gastric parietal cells to prevent the secretion of hydrogen ions. This mechanism of action is different from that of H2-blockers, which block the action of histamine on the histamine H2-receptors of parietal cells to decrease their production of acid. The proton pump inhibitor is often provided as a tablet or capsule, often containing delayed release, enteric-coated granules that survive the low pH of the stomach, and release at higher pH in the intestines, as proton pump inhibitors are acid labile. In the more neutral condition of the small intestines, the proton pump inhibitor is rapidly absorbed into the bloodstream. The strength of the proton pump inhibitor usually ranges from 10 mg to 60 mg, and is often taken 1 to 2 times per day. Lansoprazole and omeprazole are the most commonly prescribed proton pump inhibitors, although other proton pump inhibitors include aripiprazole, dexlansoprazole, esomeprazole, pantoprazole, and rabeprazole. While many proton pump inhibitors are benzimidazole derivatives, newer proton pump inhibitors include imidazopyridine derivatives. Proton pump inhibitors, such as lansoprazole, often have inter-individual and intra-individual differences in pharmacokinetic profiles and can be affected by differences in cytochrome P450 enzyme genotypes; polymorphisms including those of CYP2C19 and CYP3A.

Antibiotics are given concomitantly with the proton pump inhibitor during *Helicobacter pylori* eradication therapy. At least two different antibiotics are recommended as part of *Helicobacter pylori* eradication therapy to reduce the risk of treatment failure and antibiotic resistance. The most commonly prescribed *Helicobacter pylori* triple therapy includes amoxicillin, clarithromycin, and either lansoprazole or omeprazole, each as a separate, individual tablet or capsule. Amoxicillin is a broad antimicrobial beta-lactam that inhibits the synthesis of the bacterial cell wall in replicating bacteria. Amoxicillin is bactericidal for both gram-positive and gram-negative bacteria and is destroyed by beta-lactamase produced from both types of bacteria. Clarithromycin is an advanced-generation macrolide antibiotic with a broad in vitro antimicrobial spectrum. It interferes with protein synthesis in bacteria. Clarithromycin is rapidly and nearly completely absorbed from the gastrointestinal tract and has extensive diffusion in the tissues and bodily fluids. It forms a microbiologically active primary metabolite, 14-(R)-hydroxyclarithromycin, primarily by the cytochrome, CYP3A.

If a patient is believed to be resistant to clarithromycin, an alternative antibiotic may be prescribed, such as tetracycline. Tetracycline is another broad-spectrum polyketide antibiotic that inhibits protein synthesis in bacteria. Metronidazole is a nitroimidazole antibiotic that inhibits nucleic acid synthesis primarily in anaerobic bacteria. However, metronidazole is less used, perhaps because it appears to be somewhat mutagenic and carcinogenic.

The *Helicobacter pylori* triple therapy regimen generally lasts for 7 to 14 days, and is preferably 10 or 14 days. It is very common for a physician to prescribe 500 mg amoxicillin capsules, 500 mg clarithromycin tablets, and 30 mg lansoprazole or 20 mg omeprazole delayed-release capsules as a triple therapy. These regimens include taking two amoxicillin 500 mg capsules, one 500 mg clarithromycin tablet, and one 30 mg lansoprazole or 20 mg omeprazole delayed-release capsule, administered together twice daily (in the morning and evening) for 10 or 14 days. These therapies therefore comprise eight pills per day, four in the morning and four in the evening. These pills come from 3 different prescription bottles. To provide greater convenience to physicians and patients, convenience kits, daily blister cards containing morning and night doses of these pills, have been produced. Still, these convenience kits contain 3 different pills of active ingredients, and there is some risk of accidentally taking one or more pills from the evening dose when taking pills from the morning dose, and vice versa. Moreover, the taking of 8 pills per day (112 pills over 2 weeks) for the triple therapy, not to mention if the patient is taking other medications, is a great number of pills that can lead to poor patient compliance or distress. Some patients have a gag reflex and have trouble swallowing pills.

There exists a great need for an improved *Helicobacter pylori* eradication therapy that solves the problems inherent in prior *Helicobacter pylori* eradication therapies; namely poor compliance, patient distress and confusion among a great number of different pills, which may also lead to medication dosing errors and increased side effects. The present invention fulfills this need by providing at least one proton pump inhibitor active pharmaceutical ingredient, and at least two different antibiotic active pharmaceutical ingredients, in the same solid oral dosage form. The present invention provides the advantage of greatly reducing the number of pills administered in a *Helicobacter pylori* eradication regimen. Preferably, only 1 to 3 of these pills are taken in the morning and evening, for a preferable total of 2 to 6 pills taken per day, thus greatly improving patient compliance in a regimen lasting up to 14 days. Since each of these pills are identical, a single bottle can contain them to avoid confusion and medication errors. The present invention also provides new formulations and methods of improving stability of these active pharmaceutical ingredients, thereby assuring the identity, strength, quality, purity, potency, and safety of the solid dose drug product of the invention. At least one antibiotic active pharmaceutical ingredient is encapsulated independently from at least one other antibiotic active pharmaceutical ingredient within the same solid oral dosage form. The present invention improves the standard of patient care in *Helicobacter pylori* eradication therapy and provides therapies ideally suited for the different metabolic needs of patients.

DETAILED DESCRIPTION OF THE INVENTION

Past regimens of *Helicobacter pylori* eradication therapy consist of numerous different pills taken orally for up to 14 days, e.g., a total of 112 pills in 2 weeks, which causes inconvenience, distress, and poor patient compliance. The present invention provides new formulations of *Helicobacter pylori* eradication therapy in a single solid oral dosage form, along with methods of preparation and methods of medical use, which greatly reduces the total number of pills taken (e.g., by one-half to one-quarter) while maintaining efficacy.

In its preferred embodiment, the invention is a solid oral dosage form for the treatment of patients with at least one of *Helicobacter pylori* infection and/or duodenal ulcer disease. The duodenal ulcer disease can be active or can be recent; e.g., the patient can have a one-year history of a duodenal ulcer. This invention can also be used for patients suspected of having an *Helicobacter pylori* infection without confirmation. This invention can also be used for patients having ailments other than duodenal ulcer disease caused by an *Helicobacter pylori* infection. The said solid oral dosage form includes at least one proton pump inhibitor active pharmaceutical ingredient and at least two different antibiotic active pharmaceutical ingredients. The solid oral dosage form further includes at least one pharmaceutically acceptable excipient ingredient. Embodiments of this invention can include any number of excipient ingredients and/or percent weight/weight of these excipient ingredients. Excipient ingredients are selected from the classes of excipients including, but not limited to, antiadherents, binders, coatings, capsule shell-comprising excipients, nanoparticles, chelators, buffering agents, acid reacting excipients, alkaline reacting excipients, disintegrants, fillers, diluents, colors, lubricants, glidants, preservatives, sorbents, flavors, sweeteners, carriers, solvents, surfactants, and any mixtures and combinations thereof; and can include lipids, liposomes, glycoproteins, proteins, carbohydrates, starches, waxes, and polymers.

The at least one proton pump inhibitor active pharmaceutical ingredient is selected from the class of proton pump inhibitors including, but not limited to, lansoprazole, omeprazole, omeprazole magnesium, aripiprazole, dexlansoprazole, esomeprazole, esomeprazole magnesium, esomeprazole sodium, esomeprazole strontium, pantoprazole, pantoprazole sodium, rabeprazole, rabeprazole sodium, and any salts, solvates, polymorphs, racemic mixtures, enantiomers, derivatives, mixtures and combinations thereof. The at least one proton pump inhibitor can therefore be a benzimidazole derivative or a imidazopyridine derivative. The at least one proton pump inhibitor active pharmaceutical ingredient is preferably included in enteric-coated pellets and/or enteric-coated granules within same said solid oral dosage form. Most proton pump inhibitors are labile in stomach acid, so the enteric-coating of their granules/pellets ensures release at the higher, more neutral pH of the intestines where the proton pump inhibitor is rapidly absorbed. In order to provide enteric-coated granules or pellets of proton pump inhibitor, the solid oral dosage form further includes at least one pharmaceutically acceptable excipient ingredient comprising the enteric coating, and is commonly an acrylic-polymer coating of some type. The following are nonlimiting examples of enteric-coated granules and pellets of proton pump inhibitor. These examples can optionally include alkaline reacting compounds as excipients in the active ingredient core or active ingredient layer that can help stabilize the proton pump inhibitor and/or help with its release.

A nonlimiting example of ingredients used in a formulation of enteric-coated granules or pellets of proton pump inhibitor include lansoprazole and/or omeprazole active pharmaceutical ingredient and the excipient ingredients: crospovidone, hypromellose, lactose, magnesium stearate, mannitol, meglumine, methacrylic acid copolymer, poloxamer, povidone and triethyl acetate. The methacrylic acid copolymer serves as the enteric-coating surrounding the inner core comprised of at least one proton pump inhibitor active pharmaceutical ingredient (e.g., lansoprazole and/or omeprazole) and the other excipients. There is preferably a separating layer between the inner core and enteric coating.

Another nonlimiting example of ingredients used in a formulation of enteric-coated granules or pellets of proton pump inhibitor include lansoprazole and/or omeprazole active pharmaceutical ingredient and the excipient ingredients: hydroxypropyl cellulose, low substituted hydroxypropyl cellulose, colloidal silicon dioxide, magnesium carbonate, methacrylic acid copolymer, starch, talc, sugar sphere, sucrose, polyethylene glycol, polysorbate 80, and titanium dioxide. The enteric coated pellets are preferably multi-layered or multi-coated starting from the small sugar sphere that serves as a small sugar bead or seed. Each layer or coat is generally applied as a solution of ingredients and solvent in the form of a mist from which the solvent evaporates or is dried off, thereby, leaving the ingredients behind on the sphere. Starting from the center is the tiny, sugar-containing bead core (e.g., a small sugar bead); followed by a separating layer or coat that can include hydroxypropyl cellulose; a drug loaded layer or coat including at least one proton pump inhibitor active pharmaceutical ingredient (e.g., lansoprazole and/or omeprazole) and at least one pharmaceutically acceptable excipient ingredient (e.g., a binding agent, etc.); another separating layer or coat that can include hydroxypropyl cellulose; and an enteric coating layer that can include an acrylic coating (e.g., methacrylic acid copolymer).

The at least two different antibiotic active pharmaceutical ingredients (biocides) of the invention are selected from the classes of antibiotics including, but not limited to, polyketide antibiotics; macrolide antibiotics, including, but not limited to, clarithromycin, erthythromycin, azithromycin, dirithromycin, roxithromycin, telithromycin, carbomycin A, josamycin, kitasamycin, midecamycin, oleandomycin, solithromycin, spiramycin, troleandomycin; beta-lactam antibiotics; penicillin drugs including, but not limited to amoxicillin, ampicillin, talampicillin, bacampicillin, lenampicillin, mezlocillin, sultamicillin, temocillin; cephem/cephalosporin antibiotics including, but not limited to, cefaclor, cefadroxil, cefalexin, cefpodoxime proxetil, cefixime, cefdinir, ceftibuten, cefotiam hexetyl, cefetamet pivoxil, cefuroxime axetil; penem antibiotics including, but not limited to, faropenem, ritipenem; monobactam antibiotics; sulfonamide antibiotics; lincosamide antibiotics including, but not limited to, lincomycin or clindamycin; aminoglycoside antibiotics including, but not limited to paromomycin; tetracycline antibiotics including, but not limited to, tetracycline, minocycline, doxycycline; quinolone antibiotics including fluoroquinolone antibiotics, but not limited to, ofloxacin, levofloxacin, norfloxacin, enoxacin, ciprofloxacin, lomefloxacin, tosufloxacin, fleroxacin, sparfloxacin, temafloxacin, nadifloxacin, grepafloxacin, baloflaxacin, prulifloxacin, pazufloxacin; nitroimidazole antibiotics including, but not limited to, metronidazole, tinidazole; nitrofuran antibiotics including, but not limited to, nitrofurantoin, furazolidone, nifurtoinol; rifamycin antibiotics including, but not limited to, rifampicin, rifabutin, rifapentine, rifaximin; glycopeptide antibiotics including, but not limited to ramoplanin; and any salts, solvates, polymorphs, racemic mixtures, enantiomers, derivatives, mixtures and combinations thereof. Although most antibiotics effective against Gram-negative bacteria, e.g., *Helicobacter pylori*, can be used, the at least two different antibiotic active pharmaceutical ingredients preferably include amoxicillin and clarithromycin and/or tetracycline. Metronidazole may also be used or substituted for one of these preferred antibiotic active pharmaceutical ingredients.

Some antibiotics are known to affect the pharmacokinetics of proton pump inhibitors, and vice versa, especially in patients known as poor metabolizers based on their polymorphs of certain cytochrome P450 enzymes, such as CYP3A. This is true of clarithromycin and lansoprazole whose metabolisms involve CYP3A. Doses of clarithromycin and lansoprazole can slow their own metabolism and the metabolism of each other, and may negatively affect their bioavailability; whereas, the pharmacokinetics of amoxicillin is affected much less, if at all, by these other active pharmaceutical ingredients. While a patient's age may have little influence on the pharmacokinetics of amoxicillin, patient's age can influence the pharmacokinetics of lansoprazole and clarithromycin.

It was decided to experiment with different solid dosage forms containing proton pump inhibitor and different antibiotics by encapsulating independently at least one antibiotic in the same solid oral dosage form also containing at least one proton pump inhibitor and at least one additional antibiotic. The goal of these experiments was to vary the independent encapsulation of at least one antibiotic ingredient in the solid oral dosage form to vary the release time and bioavailability of that antibiotic (e.g., clarithromycin), with respect to the other active ingredients (e.g., lansoprazole and amoxicillin) and with respect to the characteristics of certain patients. For instance, the release rate of clarithromycin may be chosen as faster for homozygous extensive metabolizers than for heterozygous extensive metabolizers, and chosen as delayed for poor metabolizers and older patients and those with renal impairment. In this manner the pharmacokinetics or bioavailability of that antibiotic, and its pharmacokinetic interactions with other active ingredients, can be modulated and customized for different patient groups, and provide additional different functions than *Helicobacter pylori* eradication therapy convenience kits. There is currently no *Helicobacter pylori* eradication therapy available with the elements of a proton pump inhibitor and antibiotics in the same pill, nor the element of an independently encapsulated antibiotic ingredient in the same pill. There is currently no *Helicobacter pylori* eradication therapy that can be tailored to a patient's drug metabolizing enzymes. The perceived benefits of this solid oral dosage form would take place after oral administration.

However, the independent encapsulation of at least one antibiotic ingredient in the solid oral dosage form needed for these experiments had unexpected benefits unrelated to the goal of these experiments; unexpected benefits that occurred before oral administration. It was inadvertently found that by encapsulating at least one antibiotic ingredient in the solid oral dosage form (e.g., clarithromycin) independently from other (antibiotic) active ingredients, the stability of the formulation was greatly enhanced over formulations that did not have this independent encapsulation within the solid oral dosage form. These unexpected results can provide for longer shelf-life for this improved *Helicobacter pylori* eradication therapy, with lower impurities/degradants over this shelf-life. It appears that this independent encapsulation may provide protection against chemical reaction with other active pharmaceutical ingredients (e.g., amoxicillin), such as with one or more active moieties (e.g., amino, hydroxy, carbonyl and carboxyl groups, etc.), which can otherwise lead to the formation of impure intermediates that have little or no pharmacological activity or may be toxic. This independent encapsulation may also help protect against other factors including oxidation, residual organic solvents and moisture, to improve stability of one or more active ingredients of the solid oral dosage form. Due to the technical challenges of independently encapsulating the at least one antibiotic ingredient in the solid oral dosage form of this *Helicobacter pylori* eradication therapy, production costs are increased and more complex manufacturing machinery are required, and this would not be obvious for one of ordinary skill in the art to try.

The discovery of improved stability of these active pharmaceutical ingredients helps assure the identity, strength, quality, purity, potency, and safety of the solid dose drug product of the invention.

The solid oral dosage form includes a structure selected from the class of solid oral dosage forms including, but not limited to, capsules, tablets, coated capsules, coated tablets, multi-coated capsules, multi-coated tablets, multi-compartment capsules, segmented capsules, multi-compartment tablets, segmented tablets, multi-layer tablets, capsules with sub-capsule(s), capsules or tablets with sub-tablet(s), and any combinations or derivatives thereof. Coatings can include enteric coatings and non-enteric coatings. A non-limiting example of excipients that can comprise a capsule shell include: gelatin, titanium dioxide, silicon dioxide, iron oxide, sodium lauryl sulfate, and dyes, such as FD&C Blue No. 1, FD&C Red No. 40, and FD&C Yellow No. 6. A nonlimiting example of excipients that can comprise capsule fillers are cellulose microcrystalline and magnesium stearate. A nonlimiting example of excipients that can comprise tablet fillers include: hypromellose, hydroxypropyl cellulose, colloidal silicon dioxide, croscarmellose sodium, magnesium stearate, microcrystalline cellulose, and povidone. A nonlimiting example of excipients that can comprise a tablet coat include: propylene glycol, sorbic acid, sorbitan monooleate, titanium dioxide, vanillin, and D&C Yellow No. 10.

According to the invention, the solid oral dosage form includes at least one proton pump inhibitor active pharmaceutical ingredient and at least two different antibiotic active pharmaceutical ingredients. At least one of said at least two different antibiotic active pharmaceutical ingredients is encapsulated independently from said at least one other antibiotic active pharmaceutical ingredient of said at least two different antibiotic active ingredients preferably in at least one separate sub-compartment, segment, layer, sub-capsule, coated sub-tablet/large pellet or coated granule/pellet within same said solid oral dosage form.

The following preferred embodiment examples of a solid oral dosage form include up to 15 mg of lansoprazole and/or up to 10 mg of omeprazole, up to 250 mg clarithromycin, and up to 500 mg amoxicillin, per capsule or tablet. The following preferred embodiment examples also include pharmaceutically acceptable excipient ingredients. A *Helicobacter pylori* eradication therapy according to these examples would consist of the administration of two such solid oral dosages in the morning and evening for 7 to 14 days. Proton pump inhibitors other than lansoprazole and/or omeprazole, and antibiotics other than clarithromycin and/or amoxicillin, can be substituted in these preferred embodiments so that these preferred embodiment examples are not meant to be limiting. For instance, clarithromycin may be replaced by a fluoroquinolone antibiotic or tetracycline antibiotic. The quantity or dose of each active pharmaceutical ingredient is also not meant to be limiting, and can vary according to the patient type, as can one or more of the excipient ingredients and their quantities.

In a first preferred embodiment, this solid oral dosage form includes the structure of a capsule containing coated agglomerates (e.g., coated granules and/or coated pellets) of clarithromycin, enteric-coated proton pump inhibitor granules (e.g., lansoprazole and/or omeprazole), and amoxicillin powder and/or compact flakes or granules or agglomerates of amoxicillin. The coated agglomerates (e.g., coated granules and/or coated pellets) of clarithromycin are preferably coated with a polymer. This polymer can be acrylic-based, including, but not limited to, methacrylic acid copolymer. Alternatively, this coating can include a pharmaceutical glaze (e.g., a shellac coating) instead of or in addition to a polymer. The desired coating excipients of the clarithromycin coated granules or coated pellets are chosen such that clarithromycin is protected from reacting with amoxicillin, and may also be chosen to control the release of clarithromycin for different patient metabolizers. The coated pellets of clarithromycin are preferably multi-layered or multi-coated starting from a small sugar sphere that serves as a small sugar bead or seed. Each layer or coat is generally applied as a solution of ingredients and solvent in the form of a mist from which the solvent evaporates or is dried off, thereby, leaving the ingredients behind on the sphere. Starting from the center is the tiny, sugar-containing bead core (e.g., a small sugar bead); followed by a separating layer or coat that can include hydroxypropyl cellulose; the clarithromycin loaded layer or coat including at least one pharmaceutically acceptable excipient ingredient (e.g., a binding agent, etc.); another separating layer or coat that can include hydroxypropyl cellulose; and the final protective coating layer that can include an acrylic-based coating (e.g., methacrylic acid copolymer) and/or a shellac coating. Alternatively, the coated clarithromycin pellet can be a clarithromycin-containing core with excipients surrounded by a separating layer, followed by the protective outer coating layer. These examples of how the coated clarithromycin pellet is structured are not meant to be limiting.

In most embodiments of the invention, at least one of the antibiotics is coated or encapsulated independent of the other antibiotic. This can include a single coating around all of that antibiotic in powder form or a single coating around agglomerates of that antibiotic. The agglomerates of that antibiotic are preferably coated as well. One aspect of this is to separate and prevent contact and interaction of that antibiotic with that of other antibiotic(s) in said solid oral dosage form. Preferably, all active ingredients are protected from contact and interaction with each other in said solid oral dosage form.

In an alternate first preferred embodiment, the amoxicillin is also in the form of coated pellets, so that the capsule includes coated pellets of amoxicillin, coated pellets of clarithromycin, and coated pellets of lansoprazole and/or omeprazole. These active ingredient are all protected from interacting with each other by means of their own protective coatings; i.e., all said active pharmaceutical ingredients are encapsulated independently from each other within same said solid oral dosage form.

In a second preferred embodiment, the solid oral dosage form includes the structure of a capsule. The contents interior to the capsule shell include amoxicillin powder and/or compact flakes, enteric-coated proton pump inhibitor granules (e.g., lansoprazole and/or omeprazole), and a sub-capsule containing clarithromycin. In an alternate second preferred embodiment, the capsule includes clarithromycin powder and/or compact flakes, enteric-coated proton pump inhibitor granules (e.g., lansoprazole and/or omeprazole), and a sub-capsule containing amoxicillin. In another alternate second preferred embodiment, this capsule includes enteric-coated proton pump inhibitor granules (e.g., lansoprazole and/or omeprazole), a sub-capsule containing clarithromycin, and a sub-capsule containing amoxicillin. The antibiotics of a sub-capsule can be in powder, agglomerate, solid, colloidal suspension, or semi-solid form, and the sub-capsule can contain granules, pellets, coated granules, or coated pellets of the antibiotic. The structure, dimensions, and composition of one or more sub-capsules can be chosen according to the needs of the patient type for the timing of release and on their metabolic phenotypes.

In a third preferred embodiment, the solid oral dosage form includes the structure of a segmented capsule. This segmented capsule is preferably segmented along its horizontal axis with one or more dividers to form one or more sub-compartments. The one or more dividers have the ability to protect one or more active ingredients on one side of the divider from interacting with one or more active ingredients on the other side of the divider. The one or more dividers can be made from the same or similar excipients comprising the capsule shell, or different excipients. Each capsule segment can contain at least one different active pharmaceutical ingredient. By being compartmentalized separately, at least two different antibiotic active pharmaceutical ingredients are protected from interacting with at least each other. In a two-segment capsule embodiment, segment one can contain enteric-coated proton pump inhibitor granules (e.g., lansoprazole and/or omeprazole) and powder or coated pellets of clarithromycin, while segment two can contain amoxicillin as powder or coated pellets. In this example, the proton pump inhibitor and clarithromycin are compartmentalized together with at least one pharmaceutically acceptable excipient ingredient, and separate from amoxicillin, within the same solid oral dosage form. In a three-segment capsule embodiment, segment one can contain clarithromycin powder, compact flakes, granules or coated pellets, segment two can contain coated pellets of lansoprazole and/or omeprazole, and segment three can contain amoxicillin powder, compact flakes, granules, or coated pellets. In this example, all active pharmaceutical ingredients can be encapsulated independently from each other within the same solid oral dosage form at least by being compartmentalized separately from each other.

In third preferred embodiments, these capsule segments can exist as separate segments that are fused together during manufacture while maintaining divisions/dividers between them; and/or these separate capsule segments are encapsulated together within a larger, outermost capsule shell. The excipients comprising each separate segment shell may be varied among the segments to allow for different release rates of active pharmaceutical ingredients (e.g., clarithromycin). For example, the segment shell containing clarithromycin powder may be thicker and comprised of different excipients than those comprising the thinner segment shell containing amoxicillin powder. The segment shell containing clarithromycin powder may be made thicker and/or made to dissolve more slowly for those patients with slower metabolisms, and made thinner and/or made to dissolve more quickly for those patients with faster metabolisms. A four-segment capsule embodiment can contain a third antibiotic, such as tetracycline (e.g., 125 mg to 250 mg), in a fourth segment to the solid oral dosage form. Or, this fourth segment can optionally include other active pharmaceutical ingredients.

In a fourth preferred embodiment, the solid oral dosage form includes the structure of a tablet. The tablet can be tableted from amoxicillin powder, fillers, coated proton pump inhibitor granules, and clarithromycin either as multiple coated granules, or one or more large coated pellets or coated sub-tablets within the primary tablet. Amoxicillin is unable to interact with clarithromycin and proton pump inhibitor because of their protective coatings in this unique tablet.

In a fifth preferred embodiment, the solid oral dosage form includes the structure of a multi-layer tablet. Each layer contains its own protective coating so that the tablet is also a multi-coated tablet. Amoxicillin is contained in a separate coated layer from clarithromycin. The proton pump inhibitor can be contained in a third coated layer. The structure, dimensions, and composition of one or more layer coatings can be chosen according to the needs of the patient type for the timing of release and their metabolic needs.

In addition to the at least one proton pump inhibitor and at least two different antibiotics, further alternate embodiments of the preferred embodiments include at least one additional type of active pharmaceutical ingredient including, but not limited to, a beta-lactamase inhibitor, a bismuth compound, and/or a histamine H2-receptor antagonist. Bismuth compounds can have weak antacid properties and temporarily help reduce discomforts from irritated tissue lining the gastrointestinal tract by coating them. The solid oral dosage form according to the invention can therefore further include at least one beta-lactamase inhibitor selected from the class of beta-lactamase inhibitors including, but not limited to, clavulanic acid, tazobactam, sulbactam, and any salts, solvates, polymorphs, racemic mixtures, enantiomers, derivatives, mixtures and combinations thereof; and/or, the solid oral dosage form can further include at least one bismuth pharmaceutical active ingredient selected from the class of bismuth compounds including, but not limited to, bismuth subcitrate, bismuth aluminate, bismuth oxide, bismuth salicylate, bismuth subgallate, bismuth tannate, bismuth phosphate, bismuth tribromphenate, bismuth subcarbonate, bismuth subnitrate, and any salts, solvates, polymorphs, racemic mixtures, enantiomers, derivatives, mixtures and combinations thereof; and/or, the solid oral dosage form can further include at least one histamine H2-receptor antagonist selected from the class of histamine H2-receptor antagonists including, but not limited to, ranitidine, cimetidine, famotidine, nizatidine, and any salts, solvates, polymorphs, racemic mixtures, enantiomers, derivatives, mixtures and combinations thereof. For example, the third preferred embodiment of the solid oral dosage form having the structure of a segmented capsule, as described above, can include an optional fourth segment that includes at least one pharmaceutically acceptable excipient ingredient and either a beta-lactamase inhibitor, a bismuth compound, or a histamine H2-receptor antagonist as an active pharmaceutical ingredient, instead of, or in addition to, tetracycline; the other three segments containing clarithromycin powder, lansoprazole granules and/or omeprazole granules, and amoxicillin powder, respectively, along with their respective excipient ingredients.

In most embodiments, said antibiotic active pharmaceutical ingredient is encapsulated together with at least one pharmaceutically acceptable excipient ingredient, and together are independently encapsulated from said at least one other antibiotic active pharmaceutical ingredient within same said solid oral dosage form. Pharmaceutically acceptable excipient ingredients can also help protect against heat, light and ultra-violet light, oxidation, and moisture. The choice of excipients can also influence the release rates of active pharmaceutical ingredients and help provide differential or controlled release rates. Still in other embodiments, this antibiotic active pharmaceutical ingredient can be encapsulated together with at least one other active pharmaceutical ingredient, and together are independently encapsulated from said at least one other antibiotic active pharmaceutical ingredient within same said solid oral dosage form. In these other embodiments, this antibiotic active pharmaceutical ingredient can be encapsulated together with a proton pump inhibitor, a beta-lactamase inhibitor, a bismuth compound, or even a histamine H2-receptor antagonist. However, it is often preferable to encapsulate the antibiotic ingredient separately from another active pharmaceutical ingredient, to safeguard against their interaction, as well. Therefore, said at least one of said at least two different antibiotic active pharmaceutical ingredients is preferably further encapsulated independently from said at least one proton pump inhibitor active pharmaceutical ingredient, or other type of active pharmaceutical ingredient, within same said solid oral dosage form.

The solid oral dosage form for the treatment of patients with at least one of *Helicobacter pylori* infection and duodenal ulcer disease includes at least one proton pump inhibitor active pharmaceutical ingredient; at least two different antibiotic active pharmaceutical ingredients; and preferably, at least one pharmaceutically acceptable excipient ingredient, including coating excipients; and optionally at least one active pharmaceutical ingredient selected from beta-lactamase inhibitors, bismuth compounds, and/or histamine H2-receptor antagonists. Of the at least two different antibiotic active pharmaceutical ingredients of this solid oral dosage form, at least one of said at least two different antibiotic active pharmaceutical ingredients is encapsulated independently from said at least the other antibiotic active pharmaceutical ingredient of said at least two different antibiotic active ingredients in order to have at least one of improved stability, longer shelf-life, maintained potency, less impurities, and lower toxicity; and/or in order to have a different release rate. A structure, dimensions, and composition of said independent encapsulation within same said solid oral dosage form can be further chosen according to the metabolizing needs/metabolizing enzyme polymorphisms of a patient/patient group. The solid oral dosage form preferably includes the structure of a capsule. The contents interior to the capsule shell preferably include at least one proton pump inhibitor active pharmaceutical ingredient in the form of coated granules and/or coated pellets and selected from lansoprazole and/or dexlansoprazole and/or omeprazole. The contents interior to the capsule shell also preferably include amoxicillin and clarithromycin, whereby at least one of amoxicillin and clarithromycin are encapsulated independently from the other by either having protective coatings in the form of coated granules and/or coated pellets, and/or are compartmentalized separately from the other by being placed and contained in a separate sub-capsule within same said solid oral dosage form, to at least protect against their interaction at least before oral administration.

Importantly, the invention includes methods for the treatment of patients with at least one of *Helicobacter pylori* infection and duodenal ulcer disease.

The invention includes a method for the treatment of patients with at least one of *Helicobacter pylori* infection and duodenal ulcer disease, which comprises orally administering, or the oral administration of, a solid oral dosage form at least once per day for at least one week. This solid oral dosage form comprises or consists of a bismuth-free pharmaceutical formulation; said bismuth-free pharmaceutical formulation consisting of one enteric-coated proton pump inhibitor active pharmaceutical ingredient wherein the one enteric-coated proton pump inhibitor is optionally in the form of enteric-coated granules or enteric-coated pellets within same said oral dosage form; one histamine H2-receptor antagonist active pharmaceutical ingredient, or a combination thereof. This bismuth-free pharmaceutical formulation further consists of at least one pharmaceutically acceptable excipient ingredient and at least two different antibiotic active pharmaceutical ingredients, wherein said at least two different antibiotic active pharmaceutical ingredients are selected from the group consisting of macrolide antibiotics and beta-lactam antibiotics and wherein at least one of said at least two different antibiotic active pharmaceutical ingredients is provided with a layer or covering; coated independent from (or encapsulated independent from), and protected from contact or interacting with, at least one other antibiotic active pharmaceutical ingredient of said bismuth-free pharmaceutical formulation at least before orally administering the solid oral dosage form and wherein the solid oral dosage form optionally further consists of at least one beta-lactamase inhibitor and optionally wherein all active pharmaceutical ingredients are protected from contact and interacting with each other within same solid oral dosage form.

In this method, the at least one pharmaceutically acceptable excipient ingredient is selected from the group consisting of antiadherents, binders, coatings, capsule shell-comprising excipients, nanoparticles, chelators, buffering agents, acid reacting excipients, alkaline reacting excipients, disintegrants, fillers, diluents, colors, lubricants, glidants, preservatives, sorbents, flavors, sweeteners, carriers, solvents, surfactants, and any mixtures and combinations thereof.

In this method, the one enteric-coated proton pump inhibitor active pharmaceutical ingredient is selected from the group consisting of lansoprazole, omeprazole, omeprazole magnesium, aripiprazole, dexlansoprazole, esomeprazole, esomeprazole magnesium, esomeprazole sodium, esomeprazole strontium, pantoprazole, pantoprazole sodium, rabeprazole, rabeprazole sodium, and any salts, solvates, polymorphs, racemic mixtures and enantiomers thereof.

In this method, the at least two different antibiotic active pharmaceutical ingredients are selected from the group consisting of clarithromycin, erthythromycin, azithromycin, dirithromycin, roxithromycin, telithromycin, carbomycin A, josamycin, kitasamycin, midecamycin, oleandomycin, solithromycin, spiramycin, troleandomycin; penicillin drugs, amoxicillin, ampicillin, talampicillin, bacampicillin, lenampicillin, mezlocillin, sultamicillin, temocillin; and any salts, solvates, polymorphs, racemic mixtures and enantiomers, mixtures and combinations thereof.

In this method, at least one of said at least two different antibiotic active pharmaceutical ingredients is replaced by or supplemented with a fluoroquinolone antibiotic or tetracycline antibiotic. For example, if patients develop resistance to an antibiotic, such as clarithromycin, one or more fluoroquinolone antibiotics, e.g., levofloxacin, moxifloxacin, or a tetracyline antibiotic may be needed to replace or supplement clarithromycin in the solid oral dosage form or outside the solid oral dosage form.

In this method, the at least one beta-lactamase inhibitor is selected from the group consisting of clavulanic acid, tazobactam, sulbactam, and any salts, solvates, polymorphs, racemic mixtures and, enantiomers, mixtures and combinations thereof.

This method further comprises the step of pharmacogenomic testing of drug metabolism enzymes of said patients prior to said orally administering the solid oral dosage form. This would generally include the pharmacogenomic testing of patients' cytochromes to determine if they are homozygous extensive metabolizers, heterozygous extensive metabolizers, or poor metabolizers for one or more active pharmaceutical ingredients in said solid oral formulation. Such testing looks at phenotypic variants of genes that express patients' cytochromes, and can employ the method and use of genetic sequencing, probing, or duplicating patients' DNA samples. This method would include a physician prescribing a formulation of the solid oral dosage form that is best compatible with said patients.

In this method, the one histamine H2-receptor antagonist is selected from the group consisting of ranitidine, cimetidine, famotidine, nizatidine, and any salts, solvates, polymorphs, racemic mixtures and enantiomers thereof.

In this method, the solid oral dosage form consists of a single tablet or single capsule structure, although other forms and structures are possible, including capsules and sub-capsules and tablets and sub-tablets, and other layers and compartmentalization arrangements.

In this method, the solid oral dosage form consists of at least two identical capsules or tablets.

In this method, the solid oral dosage form consists of three to eight identical capsules or tablets, orally administered as an at least one dose per day. Up to eight identical capsules or tablets may be needed to reduce the size of said identical capsules or tablets for pediatric, elderly, or disabled patients. The reduced size of said identical capsules or tablets will allow for easier swallowing in such patients and is meant to improve patient compliance in those instances, rather than increase the number of capsules or tablets which would otherwise reduce patient compliance.

This method includes orally administering the solid oral dosage form at least twice per day for up to three weeks, preferably before breakfast and dinner.

This method includes orally administering the solid oral dosage form twice per day for two weeks.

This method includes orally administering the solid oral dosage form twice per day for less than two weeks.

The method further comprises the step of gastrointestinal endoscopy prior to beginning said orally administering said solid oral dosage form to identify *Helicobacter pylori* infection or duodenal ulcer disease. This can involve a rapid urease test, biopsy and tissue analysis, and growing and assaying microbiological samples. Likewise, the method further comprises the step of gastrointestinal endoscopy after completing said orally administering said solid oral dosage form to confirm elimination of *Helicobacter pylori* infection.

In this method, the patients' duodenal ulcer disease is active or was at least active within the past twelve months.

The method further comprises the step of orally administering an antibiotic-free pharmaceutical preparation consisting of proton pump inhibitor active pharmaceutical ingredient, histamine H2-receptor antagonist active pharmaceutical ingredient, bismuth-containing active pharmaceutical ingredient, or a combination thereof after completing all said orally administering of said solid oral dosage form. By treating said infection with the antibiotic-containing, solid oral dosage form, an antibiotic-free pharmaceutical preparation may then be orally administered for reducing peptic secretion, painful symptoms, and or allowing ulcers to continue to heal after the infection is gone.

In this method, the at least one of said at least two different antibiotic active pharmaceutical ingredients is coated independently or separated from contact with said at least one other antibiotic active pharmaceutical ingredient of said at least two different antibiotic active ingredients in order to have at least one of improved stability, longer shelf-life, maintained potency, less impurities, lower toxicity, or a combination thereof. Ideally, all active pharmaceutical ingredients are protected from contact and interacting with each other within same solid oral dosage form.

In this method, the at least one of said at least two different antibiotic active pharmaceutical ingredients is coated independently from said at least one other antibiotic active pharmaceutical ingredient of said at least two different antibiotic active ingredients in order to have a different release rate.

In this method, the at least one of said at least two different antibiotic active pharmaceutical ingredients is coated independently from said at least one other antibiotic active pharmaceutical ingredient of said at least two different antibiotic active ingredients; a structure, dimensions, and composition of said independent coating within same said solid oral dosage form chosen according to the metabolizing needs/metabolizing enzyme polymorphisms of a patient/patient group in order to provide a release rate and onset of bioavailability directly proportionate to the extent of metabolic efficiency of said patient/patient group with a faster release and onset of bioavailability of said at least one of said at least two different antibiotic active pharmaceutical ingredients for heterozygous extensive metabolizers than for poor metabolizers, and with a faster release and onset of bioavailability of said at least one of said at least two different antibiotic active pharmaceutical ingredients for homozygous extensive metabolizers than for heterozygous extensive metabolizers.

The invention also includes a method for the treatment of patients with at least one of *Helicobacter pylori* infection and duodenal ulcer disease, said method comprising orally administering a solid oral dosage form at least once per day for at least one week. This solid oral dosage form consists of two to eight identical capsules or tablets that are bismuth-free. These two to eight identical capsules or tablets consist of one enteric-coated proton pump inhibitor active pharmaceutical ingredient, one histamine H2-receptor antagonist active pharmaceutical ingredient, or a combination thereof. These two to eight identical capsules or tablets further consist of at least one pharmaceutically acceptable excipient ingredient, and at least two different antibiotic active pharmaceutical ingredients, wherein said at least two different antibiotic active pharmaceutical ingredients are selected from macrolide antibiotics and beta-lactam antibiotics and wherein at least one of said at least two different antibiotic active pharmaceutical ingredient is protected from contact or interacting with at least one other antibiotic active pharmaceutical ingredient at least before orally administering the solid oral dosage form by being coated independent from said at least one other antibiotic active pharmaceutical ingredient of said at least two different antibiotic active ingredients within each of said two to eight identical capsules or tablets and optionally wherein said one enteric-coated proton pump inhibitor active pharmaceutical ingredient is in the form of coated granules, coated pellets, or a combination thereof.

In this method, the one enteric-coated proton pump inhibitor active pharmaceutical ingredient is in the form of coated granules, coated pellets, or a combination thereof and selected from the group consisting of lansoprazole, dexlansoprazole, omeprazole, aripiprazole, esomeprazole, pantoprazole, and rabeprazole, said one enteric-coated proton pump inhibitor active pharmaceutical ingredient is in the amount of 10 mg to 60 mg in said solid oral dosage form; and said one histamine H2-receptor antagonist is selected from the group consisting of ranitidine, cimetidine, and nizatidine in the amount of 150 mg to 800 mg or famotidine in the amount of 20 mg to 40 mg, in said solid oral dosage form.

The invention also includes a method for the treatment of patients with at least one of *Helicobacter pylori* infection and duodenal ulcer disease, said method comprises orally administering a solid oral dosage form twice per day for one to two weeks; said solid oral dosage form consisting of two to six identical single capsules that are bismuth-free, said two to six identical single capsules consisting of one enteric-coated proton pump inhibitor active pharmaceutical ingredient, wherein said one enteric-coated proton pump inhibitor active pharmaceutical ingredient is selected from lansoprazole, dexlansoprazole, and omeprazole in an amount of 20 mg to 30 mg in said solid oral dosage form. These two to six identical single capsules further consist of at least one pharmaceutically acceptable excipient ingredient, and at least two different antibiotic active pharmaceutical ingredients; wherein at least one of said at least two different antibiotic active pharmaceutical ingredient is protected from contact or interacting with at least one other antibiotic active pharmaceutical ingredient at least before orally administering the solid oral dosage form by being coated independent from said at least one other antibiotic active pharmaceutical ingredient of said at least two different antibiotic active ingredients within each of said two to six identical single capsules, said at least two different antibiotic active pharmaceutical ingredients consisting of amoxicillin and clarithromycin each in an amount of at least 500 mg in said solid oral dosage form.

The invention also includes a method for the treatment of patients with at least one of *Helicobacter pylori* infection and duodenal ulcer disease, said method comprising orally administering a solid oral dosage form at least once per day for at least one week. The solid oral dosage form consists of two to eight identical single capsules or tablets that are bismuth-free; said two to eight identical single capsules or tablets consist of one enteric-coated proton pump inhibitor active pharmaceutical ingredient in the form of coated granules, coated pellets, or a combination thereof, one histamine H2-receptor antagonist active pharmaceutical ingredient, or a combination thereof. These two to eight identical single capsules or tablets further consist of at least one pharmaceutically acceptable excipient ingredient and at least two different antibiotic active pharmaceutical ingredients; wherein said at least two different antibiotic active pharmaceutical ingredients are selected from the group consisting of macrolide antibiotics and beta-lactam antibiotics and wherein at least one of said at least two different antibiotic active pharmaceutical ingredients is protected from contact or interacting with at least one other antibiotic active pharmaceutical ingredient at least before orally administering the solid oral dosage form by being coated independent from said at least one other antibiotic active pharmaceutical ingredient within each of said two to eight identical single capsules or tablets in order to have at least one of a different release rate, improved stability, longer shelf-life, maintained potency, less impurities, lower toxicity, or a combination thereof; a coated form of said at least one of said at least two different antibiotic active pharmaceutical ingredients having a structure, dimensions, and composition chosen according to the metabolizing needs/metabolizing enzyme polymorphisms of a patient/patient group in order to provide a release rate and onset of bioavailability directly proportionate to the extent of metabolic efficiency of said patient/patient group with a faster release and onset of bioavailability of said at least one of said at least two different antibiotic active pharmaceutical ingredients for heterozygous extensive metabolizers than for poor metabolizers, and with a faster release and onset of bioavailability of said at least one of said at least two different antibiotic active pharmaceutical ingredients for homozygous extensive metabolizers than for heterozygous extensive metabolizers; and wherein all active pharmaceutical ingredients are protected from contact and interacting with each other within same said solid oral dosage form.

In this method, the one enteric-coated proton pump inhibitor active pharmaceutical ingredient in the form of coated granules, coated pellets, or a combination thereof is selected from the group consisting of lansoprazole, dexlansoprazole, and omeprazole in an amount of 20 mg to 30 mg in said solid oral dosage form, and said at least two different antibiotic active pharmaceutical ingredients consists of amoxicillin and clarithromycin each in an amount of at least 500 mg in said solid oral dosage form, wherein at least clarithromycin is in coated form in said solid oral dosage form.

Choice and amounts of pharmaceutically acceptable excipient ingredients and other methods of use and dosing of the solid oral formulation, along with other variations and embodiments of the invention described herein will now be apparent to those of skill in the art without departing from the disclosure of the invention or the coverage of the claims to follow.

What is claimed is:

1. A method for treatment of patients with at least one of *Helicobacter pylori* infection and duodenal ulcer disease, said method comprising orally administering a solid oral dosage form at least once per day for at least one week; said solid oral dosage form consisting of a bismuth-free pharmaceutical formulation; said bismuth-free pharmaceutical formulation consisting of one enteric-coated proton pump inhibitor active pharmaceutical ingredient wherein the one enteric-coated proton pump inhibitor is optionally in the form of enteric-coated granules or enteric-coated pellets within same said oral dosage form; one histamine H2-receptor antagonist active pharmaceutical ingredient, or a combination thereof; said bismuth-free pharmaceutical formulation further consisting of at least one pharmaceutically acceptable excipient ingredient and at least two different antibiotic active pharmaceutical ingredients, wherein said at least two different antibiotic active pharmaceutical ingredients are selected from the group consisting of macrolide antibiotics and beta-lactam antibiotics and wherein at least one of said at least two different antibiotic active pharmaceutical ingredients is coated independent from, and protected from contact or interacting with, at least one other antibiotic active pharmaceutical ingredient of said bismuth-free pharmaceutical formulation at least before said orally administering said solid oral dosage form and wherein the solid oral dosage form optionally further consists of at least one beta-lactamase inhibitor and optionally wherein all active pharmaceutical ingredients are protected from contact and interacting with each other within same said solid oral dosage form.

2. The method of claim 1 wherein said at least one pharmaceutically acceptable excipient ingredient is selected from the group consisting of antiadherents, binders, coatings, capsule shell-comprising excipients, nanoparticles, chelators, buffering agents, acid reacting excipients, alkaline reacting excipients, disintegrants, fillers, diluents, colors, lubricants, glidants, preservatives, sorbents, flavors, sweeteners, carriers, solvents, surfactants, and any mixtures and combinations thereof.

3. The method of claim 1 wherein said one enteric-coated proton pump inhibitor active pharmaceutical ingredient is selected from the group consisting of lansoprazole, omeprazole, omeprazole magnesium, aripiprazole, dexlansoprazole, esomeprazole, esomeprazole magnesium, esomeprazole sodium, esomeprazole strontium, pantoprazole, pantoprazole sodium, rabeprazole, rabeprazole sodium, and any salts, solvates, polymorphs, racemic mixtures and enantiomers thereof.

4. The method of claim 1 wherein said at least two different antibiotic active pharmaceutical ingredients are selected from the group consisting of clarithromycin, erthythromycin, azithromycin, dirithromycin, roxithromycin, telithromycin, carbomycin A, josamycin, kitasamycin, midecamycin, oleandomycin, solithromycin, spiramycin, troleandomycin; penicillin drugs, amoxicillin, ampicillin, talampicillin, bacampicillin, lenampicillin, mezlocillin, sultamicillin, temocillin; and any salts, solvates, polymorphs, racemic mixtures and enantiomers, mixtures and combinations thereof.

5. The method of claim 1 wherein at least one of said at least two different antibiotic active pharmaceutical ingredients is replaced by or supplemented with a fluoroquinolone antibiotic or tetracycline antibiotic.

6. The method of claim 1 wherein the at least one beta-lactamase inhibitor is selected from the group consisting of clavulanic acid, tazobactam, sulbactam, and any salts, solvates, polymorphs, racemic mixtures and, enantiomers, mixtures and combinations thereof.

7. The method of claim 1 further comprising a step of pharmacogenomic testing of drug metabolism enzymes of said patients prior to said orally administering said solid oral dosage form.

8. The method of claim 1 wherein said one histamine H2-receptor antagonist is selected from the group consisting of ranitidine, cimetidine, famotidine, nizatidine, and any salts, solvates, polymorphs, racemic mixtures and enantiomers thereof.

9. The method of claim 1 wherein said solid oral dosage form consists of a single tablet or single capsule structure.

10. The method of claim 1 wherein said solid oral dosage form consists of at least two identical capsules or tablets.

11. The method of claim 1 wherein said solid oral dosage form consists of three to eight identical capsules or tablets.

12. The method of claim 1 wherein said orally administering said solid oral dosage form is at least twice per day for up to three weeks.

13. The method of claim 1 wherein said orally administering said solid oral dosage form is twice per day for two weeks.

14. The method of claim 1 wherein said orally administering said solid oral dosage form is twice per day for less than two weeks.

15. The method of claim 1 further comprising a step of gastrointestinal endoscopy prior to beginning said orally administering said solid oral dosage form to identify *Helicobacter pylori* infection or duodenal ulcer disease.

16. The method of claim 1 further comprising a step of gastrointestinal endoscopy after completing said orally administering said solid oral dosage form to confirm elimination of *Helicobacter pylori* infection.

17. The method of claim 1 wherein said duodenal ulcer disease is active or was active within the past twelve months.

18. The method of claim 1 further comprising a step of orally administering an antibiotic-free pharmaceutical preparation consisting of proton pump inhibitor active pharmaceutical ingredient, histamine H2-receptor antagonist active pharmaceutical ingredient, bismuth-containing active pharmaceutical ingredient, or a combination thereof after completing all said orally administering of said solid oral dosage form.

19. The method of claim 1 wherein said at least one of said at least two different antibiotic active pharmaceutical ingredients is coated independently from said at least one other antibiotic active pharmaceutical ingredient of said at least two different antibiotic active ingredients in order to have at least one of improved stability, longer shelf-life, maintained potency, less impurities, lower toxicity, or a combination thereof.

20. The method of claim 1 wherein said at least one of said at least two different antibiotic active pharmaceutical ingredients is coated independently from said at least one other antibiotic active pharmaceutical ingredient of said at least two different antibiotic active ingredients in order to have a different release rate.

21. The method of claim 1 wherein said at least one of said at least two different antibiotic active pharmaceutical ingredients is coated independently from said at least one other antibiotic active pharmaceutical ingredient of said at least two different antibiotic active ingredients; a structure, dimensions, and composition of said independent coating within same said solid oral dosage form chosen according to the metabolizing needs/metabolizing enzyme polymorphisms of a patient/patient group in order to provide a release rate and onset of bioavailability directly proportionate to the extent of metabolic efficiency of said patient/patient group with a faster release and onset of bioavailability of said at least one of said at least two different antibiotic active pharmaceutical ingredients for heterozygous extensive metabolizers than for poor metabolizers, and with a faster release and onset of bioavailability of said at least one of said at least two different antibiotic active pharmaceutical ingredients for homozygous extensive metabolizers than for heterozygous extensive metabolizers.

22. A method for the treatment of patients with at least one of *Helicobacter pylori* infection and duodenal ulcer disease, said method comprising orally administering a solid oral dosage form at least once per day for at least one week; said solid oral dosage form consisting of two to eight identical capsules or tablets that are bismuth-free, said two to eight identical capsules or tablets consisting of one enteric-coated proton pump inhibitor active pharmaceutical ingredient, one histamine H2-receptor antagonist active pharmaceutical ingredient, or a combination thereof; said two to eight identical capsules or tablets further consisting of at least one pharmaceutically acceptable excipient ingredient, and at least two different antibiotic active pharmaceutical ingredients, wherein said at least two different antibiotic active pharmaceutical ingredients are selected from macrolide antibiotics and beta-lactam antibiotics and wherein at least one of said at least two different antibiotic active pharmaceutical ingredient is protected from contact or interacting with at least one other antibiotic active pharmaceutical ingredient at least before said orally administering said solid oral dosage form by being coated independent from said at least one other antibiotic active pharmaceutical ingredient of said at least two different antibiotic active ingredients within each of said two to eight identical capsules or tablets and optionally wherein said one enteric-coated proton pump inhibitor active pharmaceutical ingredient is in the form of coated granules, coated pellets, or a combination thereof.

23. The method of claim 22 wherein said one enteric-coated proton pump inhibitor active pharmaceutical ingredient is in the form of coated granules, coated pellets, or a combination thereof and selected from the group consisting of lansoprazole, dexlansoprazole, omeprazole, aripiprazole, esomeprazole, pantoprazole, and rabeprazole, said one enteric-coated proton pump inhibitor active pharmaceutical ingredient is in the amount of 10 mg to 60 mg in said solid oral dosage form; and said one histamine H2-receptor antagonist is selected from the group consisting of ranitidine, cimetidine, and nizatidine in the amount of 150 mg to 800 mg or famotidine in the amount of 20 mg to 40 mg, in said solid oral dosage form.

24. A method for the treatment of patients with at least one of *Helicobacter pylori* infection and duodenal ulcer disease, said method comprising orally administering a solid oral dosage form twice per day for one to two weeks; said solid oral dosage form consisting of two to six identical single capsules that are bismuth-free, said two to six identical single capsules consisting of one enteric-coated proton pump inhibitor active pharmaceutical ingredient, wherein said one enteric-coated proton pump inhibitor active pharmaceutical ingredient is selected from lansoprazole, dexlansoprazole, and omeprazole in an amount of 20 mg to 30 mg in said solid oral dosage form; said two to six identical single capsules further consisting of at least one pharmaceutically acceptable excipient ingredient, and at least two different antibiotic active pharmaceutical ingredients; wherein at least one of said at least two different antibiotic active pharmaceutical ingredient is protected from contact or interacting with at least one other antibiotic active pharmaceutical ingredient at least before said orally administering said solid oral dosage form by being coated independent from said at least one other antibiotic active pharmaceutical ingredient of said at least two different antibiotic active ingredients within each of said two to six identical single capsules, said at least two different antibiotic active pharmaceutical ingredients consisting of amoxicillin and clarithromycin each in an amount of at least 500 mg in said solid oral dosage form.

25. A method for the treatment of patients with at least one of *Helicobacter pylori* infection and duodenal ulcer disease, said method comprising orally administering a solid oral dosage form at least once per day for at least one week; said solid oral dosage form consisting of two to eight identical single capsules or tablets that are bismuth-free; said two to eight identical single capsules or tablets consisting of one enteric-coated proton pump inhibitor active pharmaceutical ingredient in the form of coated granules, coated pellets, or a combination thereof, one histamine H2-receptor antagonist active pharmaceutical ingredient, or a combination thereof; said two to eight identical single capsules or tablets further consisting of at least one pharmaceutically acceptable excipient ingredient and at least two different antibiotic active pharmaceutical ingredients; wherein said at least two different antibiotic active pharmaceutical ingredients are selected from the group consisting of macrolide antibiotics and beta-lactam antibiotics and wherein at least one of said at least two different antibiotic active pharmaceutical ingredients is protected from contact or interacting with at least one other antibiotic active pharmaceutical ingredient at least before said orally administering said solid oral dosage form by being coated independent from said at least one other antibiotic active pharmaceutical ingredient within each of said two to eight identical single capsules or tablets in order to have at least one of a different release rate, improved stability, longer shelf-life, maintained potency, less impurities, lower toxicity, or a combination thereof; a coated form of said at least one of said at least two different antibiotic active pharmaceutical ingredients having a structure, dimensions, and composition chosen according to the metabolizing needs/metabolizing enzyme polymorphisms of a patient/patient group in order to provide a release rate and onset of bioavailability directly proportionate to the extent of metabolic efficiency of said patient/patient group with a faster release and onset of bioavailability of said at least one of said at least two different antibiotic active pharmaceutical ingredients for heterozygous extensive metabolizers than for poor metabolizers, and with a faster release and onset of bioavailability of said at least one of said at least two different antibiotic active pharmaceutical ingredients for homozygous extensive metabolizers than for heterozygous extensive metabolizers; and wherein all active pharmaceutical ingredients are protected from contact and interacting with each other within same said solid oral dosage form.

26. The method of claim 25 wherein said one enteric-coated proton pump inhibitor active pharmaceutical ingredient in the form of coated granules, coated pellets, or a combination thereof is selected from the group consisting of lansoprazole, dexlansoprazole, and omeprazole in an amount of 20 mg to 30 mg in said solid oral dosage form, and said at least two different antibiotic active pharmaceutical ingredients consists of amoxicillin and clarithromycin each in an amount of at least 500 mg in said solid oral dosage form, wherein at least clarithromycin is in coated form in said solid oral dosage form.

* * * * *